United States Patent [19]

Goldsworthy et al.

[11] 4,390,541
[45] Jun. 28, 1983

[54] QUINOLONE DERIVATIVES AND THEIR USE IN A METHOD OF CONTROLLING AN IMMEDIATE HYPERSENSITIVITY DISEASE

[75] Inventors: John Goldsworthy, North Ascot; William J. Ross, Lightwater; John P. Verge, Henley-on-Thames, all of England

[73] Assignee: Lilly Industries Limited, London, England

[21] Appl. No.: 327,146

[22] Filed: Dec. 3, 1981

[30] Foreign Application Priority Data

Dec. 19, 1980 [GB] United Kingdom ............... 8040732

[51] Int. Cl.³ .................. A61K 31/47; C07D 215/22
[52] U.S. Cl. .................................. 424/258; 546/153
[58] Field of Search ..................... 546/153; 424/258

[56] References Cited

U.S. PATENT DOCUMENTS 4,330,549 5/1982 Friebe et al. ..................... 424/267

FOREIGN PATENT DOCUMENTS 830832 3/1960 United Kingdom .
1433774 4/1976 United Kingdom .

OTHER PUBLICATIONS

Sakamoto, et al., Chemical Abstracts, vol. 91, 20435c (1979).
Narasimhan, et al., Chemical Abstracts, vol. 95, 187030m (1981).
Ferles, et al., Chemical Abstracts, vol. 96, 122,867g (1982).
Nohara, et al., J. Med. Chem., vol. 18, No. 1, pp. 34-37 (1975).
Narasimhan, et al., Synthesis, 1979, No. 11, pp. 903-906 (1979).
Nohara, et al., J. Med. Chem., vol. 20, No. 1, pp. 141-145 (1977).
Mosti, et al., Chemical Abstracts, vol. 90, 203917k (1979).
Brajtburg, Chemical Abstracts, vol. 70, 115023x (1969).
Kotler-Brajtburg, Chemical Abstracts, vol. 70, 47251t (1969).
Gyul'budagyan, et al., Chemical Abstracts, vol. 70, 106343z (1969).
Frank, et al., Chemical Abstracts, vol. 89, 75340g (1978).

Primary Examiner—Donald G. Daus
Assistant Examiner—Diana G. Rivers
Attorney, Agent, or Firm—Leroy Whitaker; Arthur R. Whale

[57] ABSTRACT

Compounds of the following formula are described:

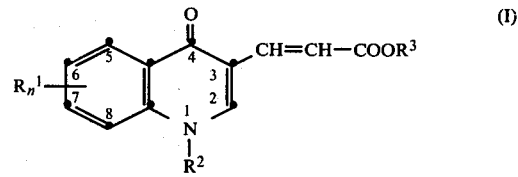

in which n is 0, 1 or 2, $R^1$ is $C_{1-4}$ alkyl, $C_{1-4}$ alkoxy, $C_{1-4}$ alkylthio, $C_{1-4}$ alkylsulphonyl, trifluoromethyl, halo or nitro, and $R^2$ and $R^3$ are each independently hydrogen or $C_{1-4}$ alkyl, and salts thereof. The compounds are useful in the treatment of immediate hypersensitivity conditions and are prepared by reaction of the appropriate formylquinolone with malonic acid, ylid or phosphonate.

6 Claims, No Drawings

QUINOLONE DERIVATIVES AND THEIR USE IN A METHOD OF CONTROLLING AN IMMEDIATE HYPERSENSITIVITY DISEASE

This invention relates to quinolone derivatives, their preparation and pharmaceutical compositions containing them.

The invention provides a compound of formula

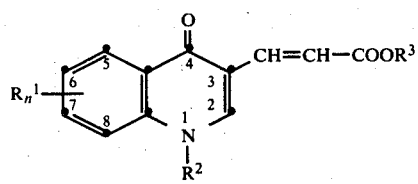

in which n is 0, 1 or 2, $R^1$ is $C_{1-4}$ alkyl, $C_{1-4}$ alkoxy, $C_{1-4}$ alkylthio, $C_{1-4}$ alkylsulphonyl, trifluoromethyl, halo or nitro, and $R^2$ and $R^3$ are each independently hydrogen or $C_{1-4}$ alkyl, and salts thereof.

We have discovered that these compounds have pharmaceutical properties and that they are especially useful in the treatment of immediate hypersensitivity conditions. Thus the invention includes a compound of formula (I) or a pharmaceutically acceptable salt thereof, for use as a pharmaceutical, more especially, for use in the treatment of immediate hypersensitivity conditions.

Reference to "$C_{1-4}$ alkyl" in formula (I) is intended to include both straight and branched chain alkyl groups, for example, methyl, ethyl, propyl, isopropyl, butyl and tert. butyl, the preferred alkyl groups being methyl and ethyl. The term "$C_{1-4}$ alkoxy" means an alkyl group such as defined above linked by an oxygen atom to the phenyl ring, and preferred groups are methoxy and ethoxy. The term "alkylthio" similarly means an alkyl group as defined above linked by a sulphur atom to the phenyl ring, a preferred group being methylthio, and the term "$C_{1-4}$ alkylsulphonyl" is an alkyl derivative as defined above linked by a sulphonyl group, a preferred group being methylsulphonyl. The term "halogen" refers to fluorine, chlorine, bromine or iodine, and is especially chlorine.

A preferred group of compounds is one in which n is 0 or 1, $R^1$ is $C_{1-4}$ alkoxy, $C_{1-4}$ alkylthio, trifluoromethyl, nitro or chloro and is in the 6 or 8 position, and $R^2$ and $R^3$ are hydrogen or methyl. More preferably n is 1, the substituent being in the 6 position, $R^2$ is methyl and $R^3$ is hydrogen.

A further preferred group of compounds is one in which n is 0 or 1, $R^1$ is trifluoromethyl or chloro in the 7 position, $R^2$ is methyl or butyl and $R^3$ is hydrogen or ethyl.

The invention also includes a method for producing a compound of formula (I) which comprises reacting a compound of formula

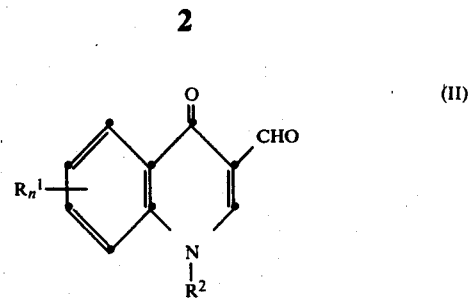

in which n, $R^1$ and $R^2$ are as defined above, with either (a) malonic acid, to produce a compound of formula (I) in which $R^3$ is hydrogen, optionally, followed by esterification to produce a compound in which $R^3$ is $C_{1-4}$ alkyl, or (b) with an appropriate ylid or phosphonate, optionally followed by deesterification to produce a compound in which $R^3$ is hydrogen. In the latter reaction, which is the Wittig reaction, or the Horner modification, suitable phosphorus ylids that may be employed are those for example of formula $R_3P=CH-COOR^3$ in which R is phenyl optionally substituted with for example $C_{1-4}$ alkyl, and suitable phosphonates include for example compounds of formula

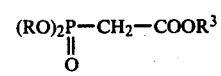

where R is $C_{1-4}$ alkyl.

Reaction (a) is preferably carried out by heating the 3-formyl quinolone with malonic acid in an inert organic solvent such as pyridine in the presence of a catalyst, for example piperidine. The reaction is preferably carried out at a temperature in the range 20° C. to 120° C. The solvent may then be removed under vacuum and the solid residue recrystallised. Reaction (b) is preferably carried out by heating the reactants in dimethylformamide (DMF) with stirring, at a temperature of, for example, from 20° C. to 100° C., then evaporating to dryness and purifying the residue.

The intermediate compounds of formula (II)

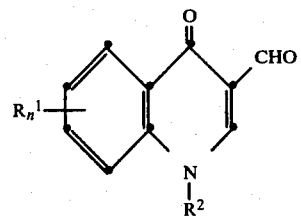

in which n, $R^1$ and $R^2$ are as defined in formula (I) above, are included as a further aspect of the invention. They can be prepared from known starting materials by conventional chemical synthetic routes.

For example in one route the compound of formula (II) where $R^2$ is alkyl is prepared by oxidising a compound of formula cyclisation and deesterification. This route can be summarised in the following scheme:

(III)

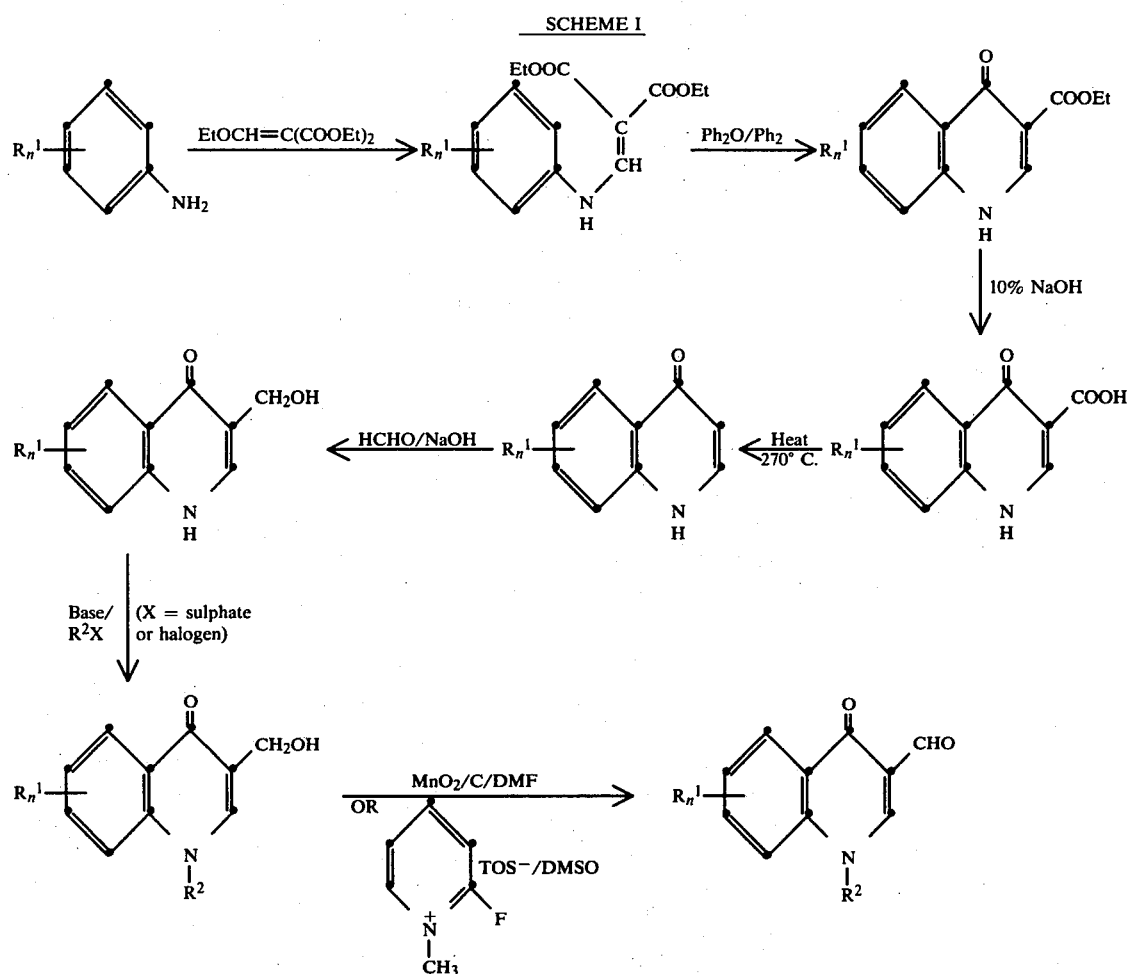

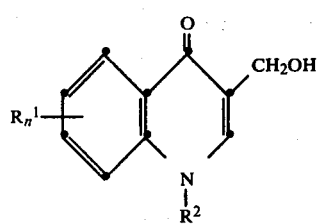

employing, for example, manganese dioxide in DMF or 1-methyl-2-fluoro-pyridinium tosylate in dimethylsulphoxide (DMSO).

Compounds of formula (III) are prepared, in their turn, from the corresponding carboxylic acid by decarboxylation followed by reaction with formaldehyde in alkali such as sodium hydroxide, followed by N-alkylation, under conditions well known in the art. The carboxylic acid derivatives can be prepared from the appropriate aniline derivative by Michael condensation with diethylethoxymethylene malonate followed by In a second method of preparing compounds of formula (II) in which $R^2$ is hydrogen, the corresponding cyano compound of formula

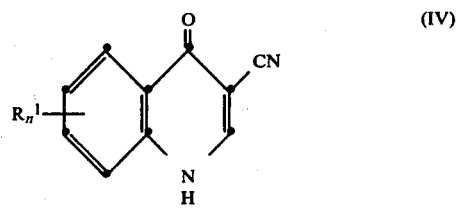

is reduced with, for example, sodium hypophosphite and Raney nickel.

Compounds of formula (IV) can be prepared by cyclisation of the appropriate anilinomethylene cyanoacetate in Dowtherm 'A' (a mixture of diphenyl ether and biphenyl). Scheme II below summarises this route.

SCHEME II

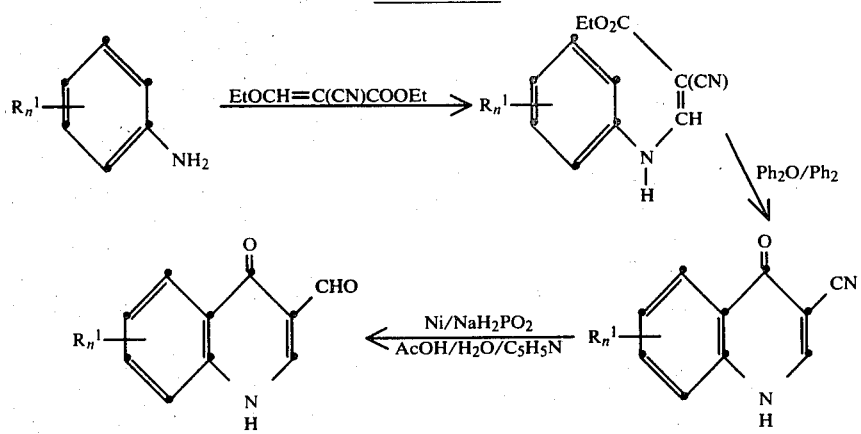

The reactions (a) and (b) above result in the production of the trans-isomer. Such trans compounds are the preferred compounds of this invention. If desired, they can be converted to the corresponding cis-isomer by chemical or photochemical methods well known in the art. For example, when $R^2$ and $R^3$ are both hydrogen, the trans compounds may be heated with a dehydrating agent such as for example polyphosphoric acid to form the lactone, followed by hydrolysis under mildly alkaline conditions to effect ring-opening. This step may be followed by esterification or N-alkylation when desired, to produce cis-isomers of compounds of formula (I).

Compounds of formula (I) in which $R^3$ is $C_{1-4}$ alkyl can be converted to the corresponding free acid in which $R^3$ is hydrogen by hydrolysis in the presence of acid such as mineral acid, for example, hydrochloric acid, and conversely, compounds in which $R^3$ is $C_{1-4}$ alkyl can be prepared by esterification of the free carboxylic group with the appropriate alcohol or by treatment with alkyl halide in the presence of base. Salts of the free acid can be prepared simply by reaction with alkali. Such salts are preferably the pharmaceutically acceptable, non-toxic, salts with suitable bases such as the alkali metal hydroxides, especially sodium and potassium hydroxides, the alkaline earth metal hydroxides especially calcium hydroxide, and amine salts. Similarly when $R^2$ is hydrogen acid addition salts can be formed in known manner, with preferably pharmaceutically acceptable acids. Apart from pharmaceutically acceptable salts other salts are also included for example, salts useful as intermediates in purification or useful for identification or characterisation.

It will also be appreciated that many of the compounds of formula (I) can be converted one to another by introduction of groups into the phenyl nucleus employing simple and well known chemical reactions. When a nitro substituent is desired, the unsubstituted compound can be nitrated with a mixture of concentrated nitric and sulphuric acid. Alkyl sulphonyl substituted compounds can be prepared from the alkylthio derivative by reaction with, for example, m-chloroperbenzoic acid.

The compounds of formula (I) and their pharmaceutically-acceptable salts, have been shown to have potential in the prophylactic and therapeutic treatment of immediate hypersensitivity diseases including asthma and in the alleviation of *status asthmaticus*. They are also of low mammalian toxicity.

This activity has been demonstrated in guinea pigs using either the "guinea pig chopped lung test" described by Mongar and Schild in the Journal of Physiology (London) 131, 207(1956) or Brocklehurst in the Journal of Physiology (London) 151, 416 (1960), or the "Herxheimer" test described in the Journal of Physiology (London) 117, 251(1952). For example compounds of formula (I) have exhibited a greater than 10 percent inhibition of mediator release in the "guinea-pig chopped lung test". In the "Herxheimer" test, which is based on an allergic broncospasm induced in guinea pigs closely resembling an asthmatic attack in man, compounds have exhibited activity at dosages ranging from 25 mg/kg to 100 mg/kg.

The compounds may be administered by various routes, although it is a special feature of the compounds that they are effective when administered orally. Thus the compounds may be administered by the oral and rectal routes, topically and parenterally or intranasally, being usually employed in the form of a pharmaceutical composition. Such a composition is prepared in a manner well known in the pharmaceutical art and normally comprises at least one active compound or salt of the invention in association with a pharmaceutically-acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus the composition can be in the form of tablets, lozenges, sachets, cachets, elixirs, suspensions, aerosols (as a solid or in a liquid medium), ointments containing for example up to 10% by weight of the active compound, soft and hard gelatine capsules, suppositories, injection suspensions and sterile packaged powders.

Some examples of suitable carriers are lactose, dextrose, sucrose, sorbitol, mannitol, starches, gum acacia, calcium phosphate, alginates, tragecanth, gelatin, syrup, methyl cellulose, methyl- and propyl-hydroxybenzoates, talc, magnesium stearate or mineral oil. The compositions of the invention may, as is well known in the art, be formulated so as to provide quick, sustained or delayed release of the active ingredient after administration to the patient.

Preferably the compositions are formulated in a unit dosage form, each dosage containing from 5 to 500 mg, more usually 25 to 300 mg, of the active ingredient. The term "unit dosage form" refers to physically discrete units suitable as unitary dosages for human subjects and animals, each unit containing a predetermined quantity of active material calculated to produce the desired therapeutic effect, in association with the required pharmaceutical carrier.

The active compounds are effective over a wide dosage range and for example dosages per day will normally fall within the range of 0.5 to 300 mg/kg. and in the treatment of adult humans, more usually in the range of from 5 to 100 mg/kg. However it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The invention is illustrated by the following Preparations and Examples, the Preparations describing the synthesis of essential intermediates for the production of compounds of formulae (I) and (II). Scheme I is illustrated by the following Preparations 1 and 2.

PREPARATION I

Freshly distilled aniline (46.5 g) and diethyl ethoxymethylene malonate (108 g) were heated together on a steam bath for two hours. The ethanol formed in the reaction was then evaporated off under vacuum to give the intermediate diethyl (anilinomethylene)malonate, m.p. 48° C.

The above intermediate was then cyclised by adding it to 1200 ml of boiling diphenyl ether, the reaction being carried out under a nitrogen atmosphere. Boiling and efficient stirring was continued until evolution of ethanol ceased (about twenty five minutes). The reaction mixture was cooled to room temperature, causing precipitation of a buff solid, and stirred for half an hour with an equal volume of n-hexane. Filtration, washing of the solid with more hexane and drying gave the compound ethyl 4(1H)-quinolone-3-carboxylate, which was recrystallised from DMF/$H_2O$, m.p. 266° C.

The ethyl 4(1H)-quinolone-3-carboxylate so obtained was boiled under reflux with 10% w/v sodium hydroxide (500 ml). A small amount of diphenyl ether impurity was allowed to steam-distil off and the mixture boiled for a further two hours. The reaction mixture was heated with decolorising charcoal (5 g) for five minutes at the boiling point, filtered and the filtrate cooled to room temperature. The filtrate was then acidified to pH 2 with concentrated hydrochloric acid, the white precipitate collected, washed with water and dried to give the corresponding acid, m.p. 256°–265° C. (with decomposition).

The 4(1H)-quinolone-3-carboxylic acid (65.5 g) was stirred and heated in a flask set in a fluidised sand bath at 270° C., under nitrogen, until no more $CO_2$ was evolved (about twenty minutes). The fused mass was allowed to cool and then dissolved in boiling ethanol (400 ml). The solution was treated with charcoal, and filtered. The filtrates were evaporated to dryness, the residue dissolved in boiling n-butanol (80 ml), the solution cooled, and an equal volume of diethyl ether then added. The cream solid was collected and dried to give 4(1H)-quinolone, m.p. 205° C.

A mixture of the 4(1H)-quinolone (41.1 g), 40% formaldehyde solution (60 ml), and 1 molar sodium hydroxide solution (360 ml) was allowed to stand for seventy two hours at 35° C. The reaction mixture was then neutralised with glacial acetic acid (21.6 g) and the solution extracted continuously with ethyl acetate (800 ml) for 6 hours. Three crops, shown by NMR and t.l.c. to be identical and the required product, 3-hydroxymethyl-4-(1H)-quinolone, were filtered off. The material had no sharp melting point, resinification occurring on heating.

Dimethyl sulphate (15.1 g) was added dropwise to a stirred solution of the 3-hydroxymethyl-4(1H)-quinolone (17.5 g) and sodium hydroxide (4.8 g) in water (50 ml) at room temperature. The exothermic reaction was controlled by water-bath cooling and the crystalline solid collected by filtration, washed with water and dried to give 1-methyl-3-hydroxymethyl-4H-quinolone, m.p. 205°–10° C. (after recrystallisation from $H_2O$/charcoal).

PREPARATION 2

In an alternative to the above N-alkylation of the hydroxymethyl derivatives, 1-n-butyl-3-hydroxymethyl-7-trifluoromethyl-4-(1H)-quinolone was prepared by adding a solution of 3-hydroxymethyl-7-trifluoromethyl-4(1H)-quinolone (30 g) in 1 liter of dry DMF to sodium hydride (3.36 g) in a little DMF (effervescence), and the mixture stirred at 70° C. for one hour. Iodobutane (38.64 g) was then added dropwise and stirring at 70° C. was continued for a further ninety minutes, when t.l.c. showed the reaction to be complete.

The DMF was removed in vacuo, the residual yellow oil partitioned between water and chloroform, the organic extracts washed with water, dried over magnesium sulphate, filtered and the solvent removed to give a sticky brownish solid. Recrystallisation from ethyl acetate and washing with diethyl ether gave the required compound as white crystals, m.p. 155°–158° C.

The 6,7-dimethyl compound, m.p. 142°–143° C., was also prepared by this method.

EXAMPLE 1

1-Methyl-3-formyl-4(1H)-quinolone

The 1-methyl-3-hydroxymethyl-4(1H)-quinolone from preparation 1 (18.9 g) was dissolved in DMF (300 ml) and activated manganese dioxide (280 g), added. The mixture was stirred at 80° C. for 16 hours, after which t.l.c. showed the reaction to be complete. The reaction mixture was filtered, the filtrates evaporated to dryness, and the solid residue washed with water to give the desired product 1-methyl-3-formyl-4(1H)-quinolone, m.p. 210°–212° C.

EXAMPLE 2

1-Methyl-3-formyl-6-trifluoromethyl-4(1H)-quinolone

In a modification, an alternative to the use of activated manganese dioxide as oxidant as in Example 1 is the use of 1-methyl-2-fluoropyridinium tosylate as illustrated in this example. (Reference: Mukaiyama et al Chemistry Letters, 369 (1978) (Japan)).

To a solution of 1-methyl-2-fluoropyridinium tosylate (3.7 g) in dimethylsulphoxide (DMSO) (20 ml) was added 1-methyl-3-hydroxymethyl-6-trifluoromethyl-4(1H)-quinolone(2.57g) followed by triethylamine (2.7 g), under a nitrogen atmosphere. The temperature rose from room temperature to 45° C. and was controlled by water-bath cooling. The reaction mixture was stirred for one hour at room temperature and then heated on a water bath at 75° C. for two hours.

The DMSO was removed by evaporation and water (50 ml) added to the residue to precipitate a pinkish crystalline solid, which was collected, washed with water, and dried.

Recrystallisation from DMF/H$_2$O gave the compound 1-methyl-3-formyl-6-trifluoromethyl-4(1H)-quinolone, m.p. 205° C.

EXAMPLES 3–13

The following compounds were prepared by the methods of Examples 1 or 2.

| | m.p. (°C.) |
|---|---|
| 1-methyl-3-formyl-6-methoxy-4(1H)-quinolone | 228–232 |
| 1-methyl-3-formyl-6-n-butoxy-4(1H)-quinolone | 159 |
| 1-methyl-3-formyl-6-n-butyl-4(1H)-quinolone | 164–166 |
| 1-methyl-3-formyl-6-methylthio-4(1H)-quinolone | 220–222 |
| 1-methyl-3-formyl-7-chloro-4(1H)-quinolone | 266 |
| 1-methyl-3-formyl-6-nitro-4(1H)-quinolone | 268–272 |
| 1-methyl-3-formyl-6-chloro-4(1H)-quinolone | 250 |
| 1-methyl-3-formyl-6-isopropyl-4(1H)-quinolone | 173–175 |
| 1-methyl-3-formyl-8-chloro-4(1H)-quinolone | 224–226 |
| 1-n-butyl-3-formyl-7-trifluoromethyl-4(1H)-quinolone | 148–150 |
| 1-n-butyl-3-formyl-6,7-dimethyl-4(1H)-quinolone | 168–170 |

EXAMPLE 14

Trans 1-methyl-4(1H)-quinolone-3-acrylic acid

A mixture of 1-methyl-3-formyl-4(1H)-quinolone (5.61 g) and malonic acid (4.5 g) in pyridine (45 ml) with 3 drops piperidine was heated on a steam-bath for two hours. The pyridine was removed in vacuo and the solid residue washed with water and dried. Recrystallisation from DMF/H$_2$O gave the title compound. NMR confirmed the structure as pure trans-isomer, m.p. 248°–250° (with decomposition).

EXAMPLE 15–26

The following compounds of formula I were prepared following the procedure of Example 14:

| | m.p. (°C.) |
|---|---|
| 1-methyl-6-methoxy-4(1H)-quinolone-3-acrylic acid | 270–275 |
| 1-methyl-6-chloro-4(1H)-quinolone-3-acrylic acid | 235–240 |
| 1-methyl-6-n-butoxy-4(1H)-quinolone-3-acrylic acid | 250–254 |
| 1-methyl-6-trifluoromethyl-4(1H)-quinolone-3-acrylic acid | 262–264 |
| 1-methyl-6-n-butyl-4(1H)-quinolone-3-acrylic acid | 218–222 |
| 1-methyl-6-iso-propyl-4(1H)-quinolone-3-acrylic acid | 245–247 |
| 1-methyl-6-methylthio-4(1H)-quinolone-3-acrylic acid | 278–282 |
| 1-methyl-8-chloro-4(1H)-quinolone-3-acrylic acid | 260–264 |
| 1-methyl-7-chloro-4(1H)-quinolone-3-acrylic acid | 291–293 |
| 1-methyl-6-nitro-4(1H)-quinolone-3-acrylic acid | 270–272 |
| 1-n-butyl-7-trifluoromethyl-4(1H)-quinolone-3-acrylic acid | 210–212 |
| 1-n-butyl-6,7-dimethyl-4(1H)-quinolone-3-acrylic acid | 238–240 |

EXAMPLE 27

Trans 1-methyl-7-chloro-4(1H)-quinolone-3-acrylic acid, ethyl ester

A solution of 1-methyl-7-chloro-4(1H)-quinolone-3-acrylic acid (3.6 g) in dry DMF (150 ml) was stirred with anhydrous sodium carbonate (4.36 g) at 70° C. for one hour. To the reaction mixture was then added diethyl sulphate (5.06 g) dropwise, and then stirring at 70° C. was continued for twelve hours.

The DMF was removed in vacuo, the residue vigorously stirred with water (200 ml) for half an hour, filtered and dried to give an off-white solid. Recrystallisation from DMF/H$_2$O gave the title compound, m.p. 235°–237° C.

EXAMPLES 28–31

The following compounds were prepared following the procedure of Example 27.

| | m.p. (°C.) |
|---|---|
| 1-methyl-6-trifluoromethyl-4(1H)-quinolone-3-acrylic acid ethyl ester | 194 |
| 1-methyl-6-chloro-4(1H)-quinolone-3-acrylic acid ethyl ester | 202–206 |
| 1-methyl-7-trifluoromethyl-4(1H)-quinolone-3-acrylic acid ethyl ester | 255–256 |
| 1-methyl-6-nitro-4(1H)-quinolone-3-acrylic acid methyl ester | 312–314 |

EXAMPLE 32

1-Methyl-3-hydroxymethyl-4(1H)-quinolone (36.8 g) was dissolved in acetic anhydride (125 ml) with a small amount of sodium acetate (0.7 g) and the solution refluxed for ninety minutes, when t.l.c. showed the reaction to be complete.

The reaction mixture was diluted with water, neutralised with 20% sodium bicarbonate solution, extracted with chloroform (3×500 ml) and the combined organic extracts backwashed with water (3×1 liter) and dried over magnesium sulphate. Filtration and evaporation of the solvent gave 1-methyl-3-acetoxymethyl-4-(1H)-quinolone as a white solid, m.p. 142°–146° C.

A solution of 1-methyl-3-acetoxymethyl-4(1H)-quinolone (prepared in A above) (29.5 g) in glacial acetic acid (57 ml) was added dropwise to concentrated sulphuric acid (440 ml) keeping the temperature below 5° C. by ice-bath cooling. To the resultant solution was added concentrated nitric acid (18 ml) dropwise, keeping the temperature below 5° C. with cooling. The reaction mixture was stirred below 5° C. for five mintutes and then poured into ice-water and made alkaline (pH 11) with 50% w/v sodium hydroxide solution (1300 ml). The precipitated yellow material was collected by filtration, washed with water and dried. A small amount 1-methyl-3-hydroxymethyl-6-nitro-4(1H)-quinolone could be recrystallised from a large volume of ethanol, m.p. 242° C.

1-Methyl-6-nitro-4(1H)-quinolone-3-acrylic acid and its methyl ester were prepared from the 3-hydroxymethyl compound by the procedure of Examples 1, 14 and 27.

Scheme II is illustrated by the following Example 33.

EXAMPLE 33

Freshly distilled aniline (27.9 g) was heated with ethyl ethoxymethylenecyanoacetate (50.7 g) on a steam bath for four hours. The ethanol formed in the reaction was removed under vacuum to give the intermediate (anilinomethylene)-cyanoacetate as a white solid, m.p. 114°–115° C.

The above intermediate was then cyclised in boiling 'Dowtherm A' (1400 ml) under a nitrogen atmosphere. After three and a half hours the reaction mixture was cooled and stirred with an equal volume of n-hexane for half an hour. The precipitated brown solid was collected, washed with more hexane, and dried to give 4-(1H)-quinolone-3-nitrile, m.p. 280° C.

The 4-(1H)-quinolone-3-nitrile (12 g) and sodium hypophosphite (16.12 g) were dissolved in a mixture of acetic acid:water:pyridine = 125 ml: 125 ml:250 ml and 4 g of Raney Nickel (W2 grade) added (Backeberg and Staskim, J.C.S. 1962, 3691). The reaction mixture was heated at 60° C. for four hours, then the hot suspension was filtered and the catalyst cake washed with warm ethanol into the filtrates. The combined filtrates and washings were evaporated to one-third of the original volume and on equal volume of water added. The precipitated solid was filtered off, washed with water and dried to give the required 3-formyl compound as a light-brown solid, m.p. 268°–270° C. (3-formyl-4(1H)-quinolone).

The following compounds were similarly prepared:

|  | m.p. (°C.) |
|---|---|
| 3-formyl-6-n-butyl-4(1H)-quinolone | 215–217 |
| 3-formyl-6-methoxy-4(1H)-quinolone | 290° C. |
| 3-formyl-6,8-dimethoxy-4(1H)-quinolone | >260° C. |

EXAMPLE 24

Trans 4(1H)-quinolone-3-acrylic acid

A solution of 3-formyl-4(1H)-quinolone (6 g) from Example 33 and malonic acid (18 g) in pyridine (300 ml) was heated on a steam bath for four hours. The reaction mixture was then evaporated down and the residue washed thoroughly with water. Recrystallisation from DMF/H₂O gave the title compound, m.p. 242°–244° C.

EXAMPLE 35

The following compound was prepared by the method of Examples 33 and 34.

|  | m.p. (°C.) |
|---|---|
| 6-n-butyl-4(1H)-quinolone-3-acrylic acid | 253–254 |

EXAMPLE 36

Trans 6-methoxy-4(1H)-quinolone-3-acrylic acid

A solution of 3-formyl-6-methoxy-4(1H)-quinolone (8.16 g) and carbethoxymethylene triphenylphosphorane (16.79 g) in dry DMF (400 ml) was stirred at 70° C. for four hours. The reaction mixture was then evaporated to dryness and the residue shaken with a water/toluene mixture. The insoluble material was filtered off, washed consecutively with water, ethanol and toluene on the sinter, dried and recrystallised from DMF/H₂O, m.p. 277°–279° C.

The resulting 6-methoxy-4(1H)-quinolone-3-acrylic acid, ethyl ester (5 g) was dissolved by warming in 10% w/v sodium hydroxide solution (60 ml) and the solution refluxed for two hours.

The reaction mixture was then treated with decolorising charcoal at the boiling point for 10 minutes, filtered, and the filtrates acidified to pH 2 with concentrated hydrochloric acid. The resultant white precipitate was collected, stirred with water (300 ml) for half an hour, collected again, washed with more water on the sinter, and dried to give the title compound, which, after recrystallisation from DMF/H₂O, melted at 260°–262° C.

EXAMPLE 37

The following compound was prepared following the procedure of Example 36.

|  | m.p. (°C.) |
|---|---|
| 6,8-dimethoxy-4(1H)-quinolone-3-acrylic acid | 215–216 |

EXAMPLE 38

The following compounds were examined in the "guinea-pig chopped lung test" referred to above and were found to exhibit a greater than 20 percent inhibition of mediator release:

4(1H)-quinolone-3-acrylic acid
1-methyl-6-methoxy-4(1H)-quinolone-3-acrylic acid
1-methyl-8-chloro-4(1H)-quinolone-3-acrylic acid
1-methyl-6-nitro-4(1H)-quinolone-3-acrylic acid
1-methyl-6-n-butyl-4(1H)-quinolone-3-acrylic acid
1-n-butyl-7-trifluoromethyl-4(1)-quinolone-3-acrylic acid.

The following formulation Examples may employ as active compound one of the compounds in Example 38 or one of the other pharmaceutical compounds of the invention.

EXAMPLE 39

Hard gelatin capsules are prepared using the following ingredients:

|  | Quantity (mg/capsule) |
|---|---|
| Active compound | 250 |
| Starch dried | 200 |
| Magnesium stearate | 10 |

The above ingredients are mixed and filled into hard gelatin capsules.

EXAMPLE 40

A tablet formula is prepared using the ingredients below:

|  | Quantity |
|---|---|
| Active compound | 250 |
| Cellulose microcrystalline | 400 |
| Silicon dioxide fumed | 10 |
| Stearic acid | 5 |

The components are blended and compressed to form tablets.

EXAMPLE 41

An aerosol solution is prepared containing the following components:

|  | Weight % |
|---|---|
| Active ingredient | 0.25 |
| Ethanol | 2.75 |
| Propellant 22 (Chlorodifluoromethane) | 70 |

The active compound is mixed with ethanol and the mixture added to the propellant 22, cooled to −30° C. and transferred to a filling device. The required amount is then fed to a stainless steel container and diluted further with a metered amount of propellant. The valve units are then fitted to the container.

We claim:

1. A compound of formula

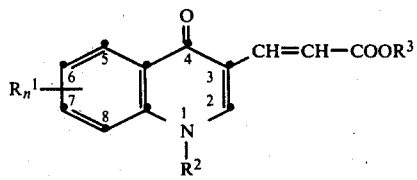

in which n is 0, 1 or 2, $R^1$ is $C_{1-4}$ alkyl, $C_{1-4}$ alkoxy, $C_{1-4}$ alkylthio, $C_{1-4}$ alkylsulphonyl, trifluoromethyl, halo or nitro, and $R^2$ and $R^3$ are each independently hydrogen or $C_{1-4}$ alkyl, and salts thereof.

2. A compound according to claim 1 in which n is 0 or 1, $R^1$ is $C_{1-4}$ alkoxy, $C_{1-4}$ alkylthio, trifluoromethyl, nitro or chloro and is in the 6 or 8 position, and $R^2$ and $R^3$ are hydrogen or methyl.

3. A compound according to claim 2 in which n is 1, the substituent being in the 6 position, $R^2$ is methyl and $R^3$ is hydrogen.

4. A compound according to claim 1 in which n is 0 or 1, $R^2$ is trifluoromethyl or chloro in the 7 position, $R^2$ is methyl or butyl and $R^3$ is hydrogen or ethyl.

5. A pharmaceutical formulation comprising a compound of formula (I) as defined in claim 1, or a pharmaceutically acceptable salt thereof, in association with a pharmaceutically acceptable carrier.

6. A method of controlling an immediate hypersensitivity disease in an animal, including a human, which comprises administering to the animal a therapeutically effective amount of a compound of formula (I) as defined in claim 1, or a pharmaceutically acceptable salt thereof.